United States Patent
Shenai-Khatkhate et al.

(10) Patent No.: US 7,166,734 B2
(45) Date of Patent: Jan. 23, 2007

(54) METHOD FOR MAKING ORGANOMETALLIC COMPOUNDS

(75) Inventors: Deodatta Vinayak Shenai-Khatkhate, Danvers, MA (US); Artashes Amamchyan, Wakefield, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 11/219,227

(22) Filed: Sep. 2, 2005

(65) Prior Publication Data

US 2006/0047132 A1    Mar. 2, 2006

Related U.S. Application Data

(60) Provisional application No. 60/606,795, filed on Sep. 2, 2004.

(51) Int. Cl.
    *C07F 5/06*    (2006.01)
(52) U.S. Cl. .................... 556/187; 556/1; 556/129; 556/170
(58) Field of Classification Search ............ 556/1, 556/129, 170, 187
    See application file for complete search history.

(56) References Cited

U.S. PATENT DOCUMENTS

| | | | |
|---|---|---|---|
| 2,954,389 A | 9/1960 | Nobis et al. ............. 260/448 |
| 3,808,207 A | 4/1974 | Shepherd et al. ........... 260/247 |
| 4,364,872 A | 12/1982 | Diefenbach ............. 260/448 A |
| 4,364,873 A | 12/1982 | Difenbach ............. 260/448 A |
| 4,740,606 A | 4/1988 | Melas ........................ 556/1 |
| 4,812,586 A | 3/1989 | Mullin et al. ............... 556/129 |
| 4,841,082 A | 6/1989 | Eidt et al. ................ 556/129 |
| 4,847,399 A | 7/1989 | Hallock et al. ............... 556/1 |
| 5,350,869 A | 9/1994 | Kanjolia et al. ............... 556/1 |
| 5,473,090 A | 12/1995 | Smit et al. ................. 556/1 |
| 5,543,537 A | 8/1996 | Eisenberg et al. .......... 556/157 |
| 5,663,390 A | 9/1997 | Giolando ..................... 556/1 |
| 5,756,786 A | 5/1998 | Power et al. ................. 556/1 |
| 5,817,847 A | 10/1998 | Giolando ..................... 556/1 |
| 6,660,874 B2 | 12/2003 | Shenai-Khatkhate et al. . 556/70 |
| 6,680,397 B2 | 1/2004 | Shenai-Khatkhate et al. .. 556/1 |
| 6,770,769 B2 | 8/2004 | Shenai-Khatkhate et al. .. 556/1 |
| 2004/0198042 A1 | 10/2004 | Shanai-Khatkhate et al. ........................ 438/680 |

OTHER PUBLICATIONS

Bradley et al., Synthesis and characterization of trialkylaluminium-dialkylamine adducts: X-ray diffraction and $^1$H NMR studies; J. Chen. Soc., Dalton Trans., 1999, pp. 3553-3558.

Eisch et al., "Organometallic Compounds of Group III. I. The Preparation of Gallium and Indium Alkyls from Organoaluminum Compounds"; Journal of the American Chemical Society, vol. 84, No. 19, Oct. 177, 1962, pp. 3605-3610.

*Primary Examiner*—Porfirio Nazario-Gonzalez
(74) *Attorney, Agent, or Firm*—S. Matthew Cairns

(57) ABSTRACT

Organometallic compounds of Group IIB and IIIA metals that are substantially pure and contain low levels of oxygenated impurities are provided. Also provided are methods of preparing such organometallic compounds.

15 Claims, No Drawings

METHOD FOR MAKING ORGANOMETALLIC COMPOUNDS

This application claims the benefit of U.S. provisional application Ser. No. 60/606,795, filed on Sep. 2, 2004.

BACKGROUND OF THE INVENTION

This invention relates generally to the field of organometallic compounds. In particular, this invention relates to the preparation of organometallic compounds suitable for use in vapor deposition and epitaxial growth of metal-containing films.

Metal films may be deposited on surfaces by a variety of means such as chemical vapor deposition ("CVD"), physical vapor deposition ("PVD"), and other epitaxial techniques such as liquid phase epitaxy ("LPE"), molecular beam epitaxy ("MBE"), chemical beam epitaxy ("CBE") and atomic layer deposition ("ALD"). Chemical vapor deposition processes, such as metalorganic chemical vapor deposition ("MOCVD"), deposit a metal layer by decomposing organometallic compounds (often referred to as "precursors") at elevated temperatures, i.e., above room temperature, either at atmospheric pressure or at reduced pressures. A wide variety of metals may be deposited using such CVD or MOCVD processes.

For semiconductor and electronic device applications, these organometallic compounds must be highly pure and be substantially free of detectable levels of both metallic impurities, such as silicon and zinc, as well as oxygenated impurities. Oxygenated impurities are typically present from the solvents, such as ethereal solvents, used to prepare such organometallic compounds, and are also present from other adventitious sources of moisture or oxygen.

Organometallic compounds of Group IIB and IIIA metals may be prepared by a variety of conventional methods. Such methods include reacting a Group IIB or IIIA metal halide with a Grignard reagent in an ethereal solvent, reacting an organo halide with a metal melt, and transalkylating a metal halide using a trialkyl aluminum, among other methods. Transalkylation reactions, such as those disclosed in U.S. Pat. Nos. 5,756,786, and 6,770,769 are particularly useful as ethereal solvents can be avoided.

When transmethylation reactions are employed using a Group IIIA metal trihalide, such as indium trihalide, and trimethyl aluminum, the reaction is not efficient with respect to the methyl groups transferred. For one mole of indium trihalide, three moles of trimethyl aluminum must be used. The resulting byproducts are also difficult to separate from the desired reaction product, trimethyl indium. Accordingly, improved methods of manufacturing Group IIB and IIIA compounds are needed.

SUMMARY OF THE INVENTION

It has been found that Group IIB and Group IIIA organometallic compounds can be prepared in high yield and in high purity by reacting a Group IIB or IIIA metal halide compound and a Group IIIA metal alkyl compound in the presence of a tertiary amine. Typically, such reaction is carried out in a hydrocarbon solvent. Organometallic compounds produced by this method are extremely pure and substantially free of oxygenated impurities.

The present invention provides a compound of the formula $R_a M^b Y_c$ (formula 1) wherein each R is independently a $(C_1-C_{10})$ organic radical, M is a Group IIB or IIIA metal, each Y is independently a $(C_1-C_4)$ carboxylate or halogen, a=1–3, b is the valence of M, c=0–2, and a+c=b; having a purity of 99.9999% and having less than 0.5 ppm of oxygenated impurities.

Also provided by the present invention is a method of preparing the above-described compound including the steps of: reacting a compound of the formula $R^1_{a'} M1^{b'} Y^1_{c'}$ (formula 2), wherein each $R^1$ is independently a $(C_1-C_{10})$ organic radical, M1 is a Group IIB or IIIA metal, each $Y^1$ is independently a $(C_1-C_4)$ carboxylate or halogen, a'=0–2, b' is the valence of M1, c'=1–3, and a'+c'=b', with a compound of the formula $R^2_x M2 Y^2_{3-x}$ (formula 3), wherein each $R^2$ is independently a $(C_1-C_{10})$ organic radical, M2 is a Group IIIA metal, each $Y^2$ is independently a $(C_1-C_4)$ carboxylate or halogen, x=1–3, in the presence of a tertiary amine or a tertiary phosphine, wherein an electronegativity of M1 $\geq$ an electronegativity of M2.

The present invention further provides a vapor delivery device including one or more of the above-described compounds. In addition, methods including one or more Group IIB or IIIA metals using the above-described compounds are contemplated by this invention.

DETAILED DESCRIPTION OF THE INVENTION

As used throughout this specification, the following abbreviations shall have the following meanings, unless the context clearly indicates otherwise: °C.=degrees centigrade; mol=moles; mmol=millimoles; b.p.=boiling point; g=gram; L=liter; μm=micron=micrometer; ppm=parts per million; ppb=parts per billion; kPa=kilopascals; and mL=milliliter.

"Halogen" refers to fluorine, chlorine, bromine and iodine and "halo" refers to fluoro, chloro, bromo and iodo. Likewise, "halogenated" refers to fluorinated, chlorinated, brominated and iodinated. "Alkyl" includes linear, branched and cyclic alkyl. Likewise, "alkenyl" and "alkynyl" include linear, branched and cyclic alkenyl and alkynyl, respectively. "Aryl" refers to any aromatic moiety, and preferably an aromatic hydrocarbon. The articles "a" and "an" refer to the singular and the plural. As used herein, "CVD" is intended to include all forms of chemical vapor deposition such as MOCVD, MOVPE, OMVPE, OMCVD and RPCVD.

Unless otherwise noted, all amounts are percent by weight and all ratios are molar ratios. All numerical ranges are inclusive and combinable in any order except where it is clear that such numerical ranges are constrained to add up to 100%.

Compounds of the formula $R_a M^b Y_c$ (formula 1), wherein each R is independently a $(C_1-C_{10})$ organic radical, M is a Group IIB or IIIA metal, each Y is independently a $(C_1-C_4)$ carboxylate or halogen, a=1–3, b is the valence of M, c=0–2, and a+c=b are provided by the present invention. In one embodiment, a=b. Suitable groups for R include alkyl, alkenyl, alkynyl and aryl. The R groups may optionally be substituted with one or more dialkylamino groups of the formula NR'R", wherein R' and R" are independently selected from $(C_1-C_4)$alkyl. By "substituted", it is meant that one or more hydrogens of the organic radical are replaced with a dialkylamino group. Typically, R is a $(C_1-C_6)$ alkyl group, optionally substituted with one or more dialkylamino groups. Exemplary R groups include, without limitation, methyl, ethyl, n-propyl, iso-propyl, n-butyl, iso-butyl, tert-butyl, iso-pentyl and neo-pentyl. Such compounds have at least one R group and may have more than one. When a compound contains more than one R group, such R groups may be the same or different. Y represents a ($C_1$–$C_4$) carboxylate or halogen. Exemplary carboxylates include formate, acetate and propionate. Typically, Y is a halogen, and more typically chloro, bromo or iodo. When more than one Y group is present in the above compound, such Y groups may be the same or different. Typically, M is zinc, cadmium, aluminum, indium or gallium. In one embodiment, M is indium or gallium. In another embodiment, a=3. In yet another embodiment, a=2 and c=1. When the compounds of formula 1 contain only R groups, the R groups may be the same or different, i.e. the compounds may be homoleptic or heteroleptic, respectively.

Exemplary compounds of formula 1 include, without limitation, trimethyl indium, triethyl indium, tri-n-propyl indium, tri-iso-propyl indium, dimethyl iso-propyl indium, dimethyl ethyl indium, dimethyl tert-butyl indium, methyl di-tert-butyl indium, methyl di-isopropyl indium, dimethyl indium chloride, dimethyl indium bromide, diethyl indium chloride, di-iso-propyl indium chloride, dimethyl indium acetate, dimethyl indium propionate, methyl indium dichloride, ethyl indium dichloride, iso-propyl indium dichloride, iso-butyl indium dichloride, allyl dimethyl indium, methyl diallyl indium, trimethyl gallium, triethyl gallium, tri-iso-propyl gallium, tri-tert-butyl gallium, dimethyl gallium chloride, dimethyl gallium bromide, diethyl gallium chloride, di-iso-propyl gallium chloride, dimethyl gallium acetate, dimethyl gallium propionate, methyl gallium dichloride, ethyl gallium dichloride, iso-propyl gallium dichloride, iso-butyl gallium dichloride, dimethyl iso-propyl gallium, diethyl tert-butyl gallium, allyl dimethyl gallium, methyl di-iso-propyl gallium, dimethyl tert-butyl gallium, dimethyl neo-pentyl gallium, tert-butyl gallium dichloride, methyl ethyl isopropyl gallium, trimethyl aluminum, triethyl aluminum, tri-n-propyl aluminum, tri-iso-propyl aluminum, tri-tert-butyl aluminum, dimethyl iso-propyl aluminum, dimethyl ethyl aluminum, dimethyl tert-butyl aluminum, methyl di-tert-butyl aluminum, methyl di-iso-propyl aluminum, dimethyl aluminum chloride, dimethyl aluminum bromide, diethyl aluminum chloride, di-iso-propyl aluminum chloride, dimethyl aluminum acetate, dimethyl aluminum propionate, methyl aluminum dichloride, ethyl aluminum dichloride, n-propyl aluminum dichloride, allyl dimethyl aluminum, methyl diallyl aluminum, dimethyl zinc, diethyl zinc, di-iso-propyl zinc, di-tert-butyl zinc, di-isobutyl zinc, allyl methyl zinc, methyl cyclopentadienyl zinc, dimethyl cadmium, diethyl cadmium, di-iso-propyl cadmium, allyl methyl cadmium, methyl zinc chloride, methyl zinc bromide, methyl zinc iodide, methyl cadmium chloride, ethyl methyl cadmium, iso-propyl methyl cadmium, and methyl cyclopentadienyl cadmium.

The compounds of formula 1 are substantially pure. In one embodiment, these compounds have a purity of 99.9999% ("6-nines"). Also, these compounds are substantially free of oxygenated impurities, i.e. they contain $\leq 0.5$ ppm of oxygenated impurities, preferably $\leq 0.1$ ppm, and more preferably $\leq 50$ ppb. Such compounds of formula 1 are particularly useful in the formation of metal films by vapor deposition used in the manufacture of electronic and optical (including optoelectronic) devices. Metal films deposited using such compounds show increased purity, decreased defects and increased electron mobility.

The compounds of formula 1 are typically prepared by a transmetallation reaction using a compound of formula 2 and an organic radical-substituted compound of formula 3 in the presence of a tertiary amine or a tertiary phosphine. Compounds of formula 2 have the formula $R^1_a M1^b Y^1_c$, wherein each $R^1$ is independently a ($C_1$–$C_{10}$) organic radical, M1 is a Group IIB or IIIA metal, each $Y^1$ is independently a ($C_1$–$C_4$) carboxylate or halogen, a'=0–2, b' is the valence of M1, c'=1–3, and a'+c'=b'. Compounds of formula 3 have the formula $R^2_x M2 Y^2_{3-x}$, wherein each $R^2$ is independently a ($C_1$–$C_{10}$) organic radical, M2 is a Group IIIA metal, each $Y^2$ is independently a ($C_1$–$C_4$) carboxylate or halogen, x=1–3. In this transmetallation reaction, one or more of the $R^2$ groups of the compound of formula 3 are transferred to the Group IIB or Group IIIA metal (M1) with the subsequent displacement of a corresponding number of $Y^1$ groups. Accordingly, M1 has an electronegativity value that is $\geq$ an electronegativity value of M2. Such reaction is typically performed using an organic solvent. Additionally, such transmetallation reaction is carried out in an oxygen-free atmosphere.

Suitable compounds of formula 2 include, without limitation, Group IIB metal dihalides, alkyl Group IIB metal halides, alkyl Group IIIA metal dihalides, dialkyl Group IIIA metal halides and Group IIIA metal trihalides. Exemplary compounds of formula 2 include cadmium dichloride, zinc dichloride, zinc dibromide, aluminum trichloride, aluminum tribromide, indium trichloride, indium tribromide, indium triiodide, indium triflouride, gallium trichloride, gallium tribromide, gallium triiodide, gallium triflouride, dimethyl aluminum chloride, dimethyl aluminum bromide, diethyl aluminum chloride, di-iso-propyl aluminum chloride, methyl aluminum dichloride, ethyl aluminum dichloride, iso-propyl aluminum dichloride, iso-butyl aluminum dichloride, iso-propyl aluminum dichloride, dimethyl gallium chloride, dimethyl gallium bromide, diethyl gallium chloride, di-iso-propyl gallium chloride, methyl gallium dichloride, ethyl gallium dichloride, iso-propyl gallium dichloride, iso-butyl gallium dichloride, dimethyl indium chloride, dimethyl indium bromide, diethyl indium chloride, di-iso-propyl indium chloride, methyl indium dichloride, ethyl indium dichloride, iso-propyl indium dichloride, and iso-butyl indium dichloride. In one embodiment, compounds of formula are zinc dichloride, zinc dibromide, indium trichloride, indium tribromide, indium triiodide, indium triflouride. gallium trichloride, gallium tribromide, gallium triiodide, and gallium triflouride. Compounds of formula 2 are generally commercially available or may be prepared from methods known to those skilled in the art.

It will be appreciated by those skilled in the art that compounds of formula 2 may include sesqui-Y-substituted compounds of Group IIIA metals. Such sesqui-Y-substituted formula 2 compounds have the formula $R^1_3 M1_2 Y^1_3$, where $Y^1$ is typically halogen. While not wishing to be bound by theory, these sesqui-Y-substituted compounds ("sesquihalides" where Y is a halogen, and "sesquicarboxylates" where Y is a carboxylate) are believed to be in an equilibrium with a 1:1 stoichiometric ratio mixture of compounds of the general formulae $R^1_2 M1 Y^1$ and $R^1 M1 Y^1_2$. Either or both of $R^1_2 M1 Y^1$ and $R^1 M1 Y^1_2$ may undergo a transmetallation reaction to add either one or two organic radical groups, respectively.

Any compound of formula 3 may be used in the transmetallation reaction with a compound of formula 2 provided that M1 and M2 have the same electronegativity, i.e. they are the same metal, or that M1 is more electronegative than M2. Of the Group IIB and IIIA metals, aluminum has the lowest electronegativity value (i.e. aluminum is the most electropositive) at 1.61. Aluminum can be used in the transmetallation reaction of any Group IIB or IIIA metal. Electronegativity values of other Group IIB and IIIA metals are: Zn: 1.65; Cd: 1.69; In: 1.78; and Ga: 1.81.

In one embodiment, the compound of formula 3 is an aluminum compound having the formula $R^2_z AlX_n$, wherein $R^2$ is a $(C_1-C_{10})$ organic radical, X is a halogen, z=1–3, n=0–2 and z+n=3. Typically, $R^2$ is $(C_1-C_{10})$alkyl, preferably $(C_1-C_6)$alkyl, and more preferably $(C_1-C_3)$alkyl. X is typically chlorine. Suitable aluminum compounds include, but are not limited to, trimethylaluminum, triethylaluminum, tri-n-propylaluminum, tri-iso-propylaluminum, tri-iso-butylaluminum, tri-tert-butylaluminum, tri-n-butylaluminum, tri-n-hexylaluminum, dimethyl aluminum chloride and the like. Such aluminum compounds are generally commercially available from a variety of sources or may be prepared by a variety of methods known in the literature.

In another embodiment, the compound of formula 3 is a sesqui-Y-substituted compound of a Group IIIA metal. Sesqui-Y-substituted compounds of formula 3 have the general formula $R^2_3M_2Y^2_3$, where $Y^2$ is typically halogen. In a further embodiment, a sesquihalide of formula 2, e.g. an alkyl indium sesquichloride, and a sesquihalide of formula 3, e.g. an alkyl aluminum sesquichloride, are employed in the transmetallation reaction.

Sesquihalides of formula 2 or 3 may be prepared by any suitable method, such as by combining compounds having the general formulae $R_2MY$ and $RMY_2$ in a 1:1 stoichiometric ratio mixture. Other methods for forming sesquihalides are well known to those skilled in the art or may be found in the literature.

Any tertiary amine or tertiary phosphine may suitably be used in the present invention. Suitable tertiary amines include, but are not limited to, those having the general formula $NR^4R^5R^6$, wherein $R^4$, $R^5$ and $R^6$ are independently selected from $(C_1-C_6)$alkyl, di$(C_1-C_6)$alkylamino-substituted $(C_1-C_6)$alkyl, and phenyl and wherein $R^4$ and $R^5$ may be taken together along with the nitrogen to which they are attached to form a 5–7 membered heterocyclic ring. Such heterocyclic ring may be aromatic or non-aromatic. Exemplary tertiary amines include, but are not limited to, trimethylamine, triethylamine, tri-n-propylamine, tri-n-butylamine, tri-iso-propylamine, tri-iso-butylamine, dimethylaminocyclohexane, diethylaminocyclohexane, dimethylaminocyclopentane, diethylaminocyclopentane, N-methylpyrrolidine, N-ethylpyrrolidine, N-n-propylpyrrolidine, N-iso-propylpyrrolidine, N-methylpiperidine, N-ethylpiperidine, N-n-propylpiperdine, N-iso-propylpiperidine, N,N'-dimethylpiperazine, N,N'-diethylpiperazine, N,N'-dipropylpiperazine, N,N,N',N'-tetramethyl-1,2-diaminoethane, pyridine, pyrazine, pyrimidine, and mixtures thereof. Particularly useful tertiary amines include trimethylamine, triethylamine, tri-n-propylamine, tri-iso-propylamine, and tri-n-butylamine. In one embodiment, the tertiary amine is triethylamine or tri-n-propylamine.

Exemplary tertiary phosphines include, without limitation, those of the general formula $R^7R^8R^9P$, where $R^7$, $R^8$, and $R^9$ are independently chosen from $(C_1-C_6)$alkyl, phenyl and $(C_1-C_6)$alkyl-substituted phenyl. Suitable tertiary phosphines include triethyl phosphine, tripropyl phosphine, tributyl phosphine, phenyl dimethyl phosphine, phenyl diethyl phosphine and butyl diethyl phosphine.

It will be appreciated by those skilled in the art that more than one tertiary amine or tertiary phosphine may be used in the present invention. Mixtures of a tertiary amine and a tertiary phosphine may also be used. Such tertiary amines and tertiary phosphines are generally commercially available from a variety of sources. Such tertiary amines and tertiary phosphines may be used as is or may be further purified prior to use. Such purification techniques are well known to those skilled in the art.

A wide variety of organic solvents may optionally be used in the present invention. Typically, such organic solvents do not contain oxygenated moieties such as ether linkages, and are preferably free of oxygen. Exemplary organic solvents include, but are not limited to, hydrocarbons and aromatic hydrocarbons. Suitable organic solvents include, without limitation, benzene, toluene, xylene, pentane, hexane, heptane, octane, decane, dodecane, squalane, cyclopentane, cyclohexane, cycloheptane, and mixtures thereof. It will be appreciated that more than one organic solvent may be advantageously used in the present invention. In an alternative embodiment, the tertiary amine may be used as the organic solvent. Such organic solvents are generally commercially available from a variety of sources, such as Aldrich (Milwaukee, Wis.). Such solvents may be used as is or may be purified prior to use.

Preferably, such organic solvents are deoxygenated prior to use. The solvents may be deoxygenated by a variety of means, such as purging with an inert gas, degassing the solvent in vacuo, or a combination thereof. Suitable inert gases include argon, nitrogen and helium, and typically argon or nitrogen.

The specific tertiary amine, tertiary phosphine and organic solvent used depend upon the particular compound of formula 1 desired. For example, the organic solvent and tertiary amine may be selected such that they are more volatile or less volatile than the desired compound of formula 1. Such differences in volatility provide easier separation of the desired compound from both the amine and organic solvent. The selection of the tertiary amine, tertiary phosphine and the organic solvent are well within the abilities of those skilled in the art.

In general, the tertiary amine and/or tertiary phosphine is present in an approximate stoichiometric amount to the formula 3 compound. The mole ratio of the compound of formula 2 to the compound of formula 3 may vary over a wide range, such as from 1:0.1 to 1:5, the particular mole ratio being dependent upon the compound of formula 1 desired. Another suitable range of mole ratios is from 1:0.5 to 1:2. Mole ratios greater than 1:5 are also expected to be effective. The particular compound of formula 1 obtained from the transmetallation reaction can be controlled by selection of the mole ratio of the compound of formula 2 and the compound of formula 3, i.e. the number of $Y^1$ groups replaced in the compound of formula 2 can be controlled by the number of moles of formula 3 compound used.

In one embodiment, the compound of formula 3, tertiary amine and/or tertiary phosphine and organic solvent may be combined in any order prior to reaction with the compound of formula 2. In a further embodiment, the formula 3 compound is first combined with the tertiary amine and/or tertiary phosphine to form an amine-formula 3 compound adduct or a phosphine-formula 3 compound adduct. Typically, the amine-formula 3 compound adduct or phosphine-formula 3 compound adduct may be formed at a wide variety of temperatures. Suitable temperatures for forming the adduct are from ambient to 90° C. The compound of formula 2 is then reacted with the amine-formula 3 compound adduct or phosphine-formula 3 compound adduct to form the desired compound of formula 1. Typically, the compound of formula 2 is added dropwise, either neat or as a hydrocarbon solution, to the adduct. Alternatively, the adduct may be added dropwise to the compound of formula 2, either neat or as a hydrocarbon solution. Suitable temperatures to form the compound of formula 1 are from ambient to 100° C.

In another embodiment, the compound of formula 2 may be combined with the formula 3 compound and optionally an organic solvent prior to the addition of the tertiary amine and/or tertiary phosphine. The tertiary amine and/or tertiary phosphine and optionally an organic solvent may then be added, such as by dropwise addition, to the compound of formula 2 and formula 3 compound mixture. Alternatively, the compound of formula 2 and compound of formula 3 mixture may be added, such as by dropwise addition, to the tertiary amine and/or tertiary phosphine and optionally an organic solvent.

The compounds of formula 1 may optionally be prepared in a continuous manner. For example, compound of formula 2 and the aluminum compound may be independently added in a continuous manner to a reaction vessel containing tertiary amine and/or tertiary phosphine in a suitable solvent, such as an aromatic or aliphatic hydrocarbon. The addition of the compound of formula 2 and the aluminum compound can be controlled by a variety of suitable means, such as by the use of mass flow controllers. In such a continuous process, the desired compound of formula 1 may be removed, such as by distillation, while the compound of formula 2 and the aluminum compound are being added to the reaction vessel. In a further alternative, a mixture of the compound of formula 2 and the aluminum compound may be added to the tertiary amine and/or tertiary phosphine in a suitable solvent. In such an alternative continuous process, the desired compound of formula 1 may be removed, such as by distillation, while the formula 2 compound/aluminum compound mixture is being added to the reaction vessel. Such continuous operation requires periodic or continuous replenishment of the tertiary amine and/or tertiary phosphine.

Compounds of formulae 2 and 3 may be selected such that when such compounds are combined, a sesqui-Y-substituted compound is formed. A tertiary amine and/or tertiary phosphine can then be added to such sesqui-Y-substituted compound. Alternatively, such sesqui-Y-substituted compound can be added to a tertiary amine and/or tertiary phosphine. Such reaction is optionally heated, and preferably is heated. For example, an alkyl aluminum dihalide may be used as the compound of formula 2 and a dialkyl aluminum halide may be used as the compound of formula 3. When mixed, such compounds typically form an alkyl aluminum sesquihalide of the formula $R_3Al_2X_3$, where R is alkyl and X is halogen. When such sesquihalides are contacted with a tertiary amine and/or tertiary phosphine, optionally with heating and optionally in the presence of an organic solvent, trialkyl aluminum and aluminum (III) halide are produced. Such approach is particularly suited to the production of trimethyl aluminum, triethyl aluminum, tripropyl aluminum and tributyl aluminum. Heteroleptic trialkyl aluminum compounds may also be prepared using such reaction. "Heteroleptic" refers to organometallic compounds that are unsymmetrical, i.e. not all of the groups bonded to the metal are the same.

The methods of the invention provide compounds of formula 1 in a suitably pure form and may be used as is. However, such compounds of formula 1 may be further purified by a variety of techniques, such as by distillation, sublimation, and recrystallization. The present method provides compounds of formula 1 that are substantially free ($\leq 0.5$ ppm) of metallic impurities such as silicon, germanium and tin. The compounds of formula 1 are also substantially free ($\leq 0.5$ ppm) of oxygenated impurities such as ethereal solvents and oxygenated organometallics, and preferably free of such oxygenated impurities.

In addition, the above methods allow for more efficient utilization of the transmetallation reaction. For example, conventional transmetallation reactions used to prepare trimethyl indium, which are performed in the absence of either a tertiary amine or a tertiary phosphine, use 3 moles of trimethyl aluminum for each mole of trichloroindium. According to the present method which employs either a tertiary amine or a tertiary phosphine, trimethyl indium may be prepared using 2 moles of indium trichloride and 3 moles (or even 2 moles) of trimethyl aluminum. Thus, twice as much trimethyl indium or more can be produced while using the same amount of trimethyl aluminum.

Compounds of formula 1 where M is a Group IIIA metal and including one or more halogens can be further reduced to form the corresponding hydride compounds. A wide variety of reducing agents may be used. Particularly useful reducing agents include, without limitation, borohydride reducing agents such as sodium borohydride and lithium borohydride; aluminum hydride reducing agents such as lithium aluminum hydride and $NaAlH_2(OCH_2CH_2OCH_3)_2$; borane reducing agents such as dimethylamine borane, cyclohexylamine borane, morpholine borane and alane reducing agents such as trimethylamine alane, methyl pyrrolidine alane, and dimethyl ethylamine alane.

In general, Group IIIA metal hydride compounds are prepared by reacting the Group IIIA metal halide compound of formula 1 (where Y is halogen and c≠0) with a reducing agent in an organic solvent and optionally in the presence of a tertiary amine and/or tertiary phosphine. Such reduction reactions are typically performed in an ethereal solvent, particularly an ethereal solvent having a b.p. of $\geq 175°$ C., and more particularly an ethereal solvent having a b.p. of $\geq 200°$ C. The tertiary amine or tertiary phosphine may be any of those described above. The optional tertiary amine and/or tertiary phosphine, organic solvent and reducing agent may be combined in any order prior to reaction with the Group IIIA metal halide of formula 1. The compound of formula 1 is typically added dropwise, either neat or as a hydrocarbon solution, to an amine-reducing agent and/or phosphine-reducing agent mixture. Typically, the reduction may be performed at a wide range of temperatures, such as from below ambient temperature to 90° C.

In such reduction reactions, the tertiary amine and/or tertiary phosphine is typically present in a stoichiometric amount based on the number of halogens in the compound of formula 1 to be reduced, although other suitable amounts may be used. For example, if the compound of formula 1 includes two halogens, then the tertiary amine and/or tertiary phosphine is used at twice the molar amount of the compound of formula 1. The amount of reducing agent is typically also present in a stoichiometric amount based on the number of halogens in the compound of formula 1 to be reduced, although other suitable amounts may be used.

Films of Group IIB and/or Group IIIA metals are typically deposited by first placing the desired metal compound of formula 1, i.e. source compound or precursor compound, in a delivery device (cylinder or bubbler) having an outlet connected to a deposition chamber. A wide variety of cylinders may be used, depending upon the particular deposition apparatus used. The source compound is typically maintained in the cylinder as a liquid or solid. Solid source compounds are typically vaporized or sublimed prior to transportation to the deposition chamber. The source compound is typically transported to the deposition chamber by passing a carrier gas through the cylinder. Suitable carrier gasses include nitrogen, hydrogen, and mixtures thereof. In general, the carrier gas is introduced below the surface of the source compound, and bubbles up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The typical deposition chamber temperature is from about 300° to about 1000° C., the exact temperature selected being optimized to provide efficient deposition. Optionally, the temperature in the deposition chamber as a whole can be reduced if the substrate is maintained at an elevated temperature, or if other energy such as radio frequency ("RF") energy is generated by an RF source.

Suitable substrates for deposition, in the case of electronic device manufacture, may be silicon, gallium arsenide, indium phosphide, and other suitable substrates. Such substrates are particularly useful in the manufacture of integrated circuits, light emitting diodes, optical devices and electro-optical devices.

Deposition is continued for as long as desired to produce a film having the desired properties. Typically, the film thickness will be from several hundred to several thousand angstroms or more when deposition is stopped.

The present compounds of formula 1 are useful in depositing any film including a Group IIB and/or Group IIIA metal, including alloys thereof. Suitable films include, but are not limited to, indium, indium-phosphide, indium-gallium-arsenide, indium-gallium-aluminum-phosphide, indium-gallium-arsenide-phosphide, indium-gallium-arsenide/gallium-arsenide/aluminum-gallium-arsenide, gallium-nitride, indium-gallium-nitride, indium-arsenide, indium-antimonide, indium-arsenide-bismuthide, zinc-selenide, cadmium-telluride and cadmium-mercury-telluride.

Thus, the present invention provides a method for depositing a film including a Group IIB and/or Group IIIA metal on a substrate including the steps of: a) conveying a compound of formula 1 in the gas phase to a deposition chamber containing the substrate; b) decomposing the compound of formula 1 in the deposition chamber; and c) depositing a film including the Group IIB and/or Group IIIA metal on the substrate.

The following examples are expected to illustrate various aspects of the present invention, but are not intended to limit the scope of the invention in any aspect.

EXAMPLE 1

Gallium trichloride (156 g, 0.88 mol) was dissolved in freshly degassed toluene (140 mL) and added dropwise with stirring to an adduct which was prepared by mixing degassed triethylamine (137 g, 1.36 mol) and trimethylaluminum (98 g, 1.36 mol) at 25° C. The reaction was found to be exothermic, and the reaction mass was maintained below 80° C. After completing the addition, the reaction mixture was stirred for 1 hour at 100° C. The crude product, trimethylgallium, (82 g, 81%). was obtained by fractional distillation at atmospheric pressure, as a fraction boiling at 56° C. The final product was compared with authentic sample by its analyses for the absence of organic and metallic impurities using Fourier transform nuclear magnetic resonance spectroscopy ("FT-NMR") and inductively coupled plasma optical emission spectrometry ("ICP-OES") techniques respectively.

EXAMPLE 2

Neat triethylaluminum (745 g, 6.53 mol) was added dropwise to degassed tripropylamine (944 g, 6.60 mol) at room temperature with stirring. The resulting adduct was stirred for several hours at reduced pressures and then added to neat gallium trichloride (730 g, 4.15 mol) powder. The reaction temperature was maintained below 100° C. by controlling the rate of addition. Upon complete addition, the reaction mixture was stirred for two hours at 100° C. The crude product was separated by reduced pressure distillation as a fraction boiling within 76–78° C. (60 torr, 8 kPa). The yield of final product, triethylgallium, was found to be 600 g (92%). The final product was compared with authentic sample by its analyses for the absence of organic and metallic impurities using FT-NMR and ICP-OES techniques respectively.

EXAMPLE 3

Gallium trichloride (29 g, 0.16 mol) was dissolved in degassed toluene (20 mL) and added dropwise at stirring to dimethylaluminum chloride (46 g, 0.49 mol). The reaction was found to be exothermic during the initial addition. Upon cooling, degassed triethylamine (50 g, 0.49 mol) was added dropwise to the reaction mixture. The reaction flask was then heated up for additional 1 hour at 100° C. The crude product was then distilled off at atmospheric pressure via a Vigreux column. The fraction boiling within 55–79° C. was collected as the crude product. This yielded net 17 g of material containing trimethylgallium and toluene at 8.4:1 molar ratio, according to the NMR spectrum (400-MHz). Thus, the yield of the crude trimethylgallium was 15.5 g (82%).

EXAMPLE 4

To a stirred suspension of zinc dichloride (68 g, 0.5 mol) in degassed toluene (100 mL), is added dropwise the solution of an adduct prepared by mixing trimethylaluminum (37 g, 0.51 mol), triethylamine (52 g, 0.51 mol) and toluene (60 mL). Upon complete addition, the expected product, dimethyl zinc, is expected to be distilled off at atmospheric pressure using a Vigreux column and to be obtained in high yield.

EXAMPLE 5

To a stirred suspension of cadmium dichloride (92 g, 0.5 mol) in degassed linear alkyl benzene (100 mL), is added dropwise the solution of the adduct prepared by mixing dimethylaluinum chloride (94 g, 1.01 mol), tripropylamine (145 g, 1.01 mol) and linear alkyl benzene (100 mL). Upon complete addition, the expected product, dimethyl cadmium, is expected to be distilled off at atmospheric pressure using a packed distillation column and to be obtained in high yield.

EXAMPLE 6

The products in the following table are expected to be produced using one or more of the procedures described above. The starting materials and procedure to be used are provided in the table.

| Compound of formula 2 | Compound of formula 3 | Tertiary amine/ tertiary phosphine | Product | Procedure |
|---|---|---|---|---|
| $GaBr_3$ | $Me_3Al$ | $Et_3N$ | $Me_3Ga$ | Example 1 |
| $MeGaCl_2$ | $i\text{-}Pr_3Al$ | $n\text{-}Pr_3N$ | $i\text{-}Pr_2GaMe$ | Example 2 |
| $Me_2GaCl$ | $Me_2AlCl$ | $Et_3N$ | $Me_3Ga$ | Example 3 |
| $i\text{-}BuGaCl_2$ | $Me_3Al_2Cl_3$ | $n\text{-}Pr_3N$ | $i\text{-}BuGaMe_2$ | Example 2 |
| $Et_2GaCl$ | $Me_3Al$ | $n\text{-}Pr_3N$ | $Et_2GaMe$ | Example 1 or 2 |
| $Me_3Ga_2Cl_3$ | $n\text{-}Pr_3Al$ | $EtNMe_2$ | $Me_2Ga(n\text{-}Pr)$ | Example 1 or 2 |
| $Me_2InCl$ | $i\text{-}Bu_3Al$ | $n\text{-}Pr_3N$ | $i\text{-}BuInMe_2$ | Example 2 |
| $Me_2In(OAc)$ | $Et_3Al$ | $Et_3N$ | $Me_2InEt$ | Example 1 |
| $i\text{-}PrInCl_2$ | $n\text{-}Pr_3Al$ | $t\text{-}Bu_3N$ | $i\text{-}PrIn(n\text{-}Pr)_2$ | Example 1 or 2 |
| $Et_2AlCl$ | $Me_3Al$ | $n\text{-}Pr_3N$ | $Et_2AlMe$ | Example 2 |
| $t\text{-}BuAlCl_2$ | $Et_3Al$ | $n\text{-}Bu_3N$ | $t\text{-}BuAlEt_2$ | Example 3 |
| $n\text{-}PrAl(OAc)_2$ | $Et_3Al_2I_3$ | $n\text{-}Pr_3P$ | $n\text{-}PrAlEt_2$ | Example 2 |
| $(DMAP)AlCl_2$ | $Me_3Al$ | $n\text{-}Bu_3N$ | $(DMAP)AlMe_2$ | Example 2 |
| $Et_3Al_2Cl_3$ | $i\text{-}Bu_3Al$ | $i\text{-}Pr_3N$ | $i\text{-}BuAlEt_2$ | Example 2 |
| $(DMAP)ZnCl$ | $Me_3Al$ | $n\text{-}Bu_3N$ | $(DMAP)ZnMe$ | Example 4 |
| $MeZnCl$ | $Et_3Al$ | $n\text{-}Pr_3N$ | $MeZnEt$ | Example 4 |
| $CpZnCl$ | $n\text{-}Pr_3Al$ | $n\text{-}Pr_3N$ | $CpZn(n\text{-}Pr)$ | Example 4 |
| $MeZn(OAc)$ | $Me_3Al$ | $Et_3N$ | $Me_2Zn$ | Example 4 |
| $EtCdCl$ | $Et_3Al$ | $n\text{-}Bu_3N$ | $Et_2Cd$ | Example 5 |
| $CdCl_2$ | $i\text{-}Bu_3Al$ | $n\text{-}Bu_3P$ | $i\text{-}Bu_2Cd$ | Example 5 |
| $CdCl_2$ | $Et_2AlCl$ | $n\text{-}Bu_3N$ | $Et_2Cd$ | Example 5 |

In the above table, the following abbreviations are used: Me=methyl; Et=ethyl; Pr=propyl; Bu=butyl, OAc=acetate; DMAP=dimethylaminopropyl; Cp=cyclopentadienyl; "i-"=iso; "n-"=normal; and "t-"=tertiary.

EXAMPLE 7

Indium trichloride (77 g, 0.35 mol) is dispersed in degassed linear alkyl benzene (200 mL) and to this suspension is added dropwise with stirring a mixture of methyl aluminum dichloride (40 g, 0.35 mol), dimethyl aluminum chloride (32 g, 0.35 mol) and trihexylamine (240 mL, 191 g, 0.7 mol). The reaction is expected to be moderately vigorous accompanied by heat evolution, and adequate cooling of the reaction mass and controlled addition is expected to be important in successfully carrying out the alkyl exchange. The reaction mass is heated to 90 to 100° C. for an hour following the complete addition of reagents. The by-product is expected to be a aluminum trichloride-trihexylamine complex, with small proportion (less than 10%) of methylaluminum dichloride-trihexylamine. The crude product is expected to be obtained by vacuum transfer, and to be further purified by sublimation in vacuo. Trimethylindium is expected in high yield and to contain oxygenated organic and metallic impurities at less than 0.1 ppm as analyzed by FT-NMR and/or ICP-OES techniques.

EXAMPLE 8

To a mixture of methyl indium dichloride (90 g, 0.45 mol), dimethylindium chloride (80 g, 0.45 mol), and tributylamine (85 g, 0.46 mol) is added with stirring and in a dropwise manner neat trimethylaluminum (45 mL, 34 g, 0.46 mol). The reaction is expected to be exothermic. The reaction mass is heated to 90 to 100° C. for an hour following the complete addition of reagents. The by-product is expected to be a aluminum trichloride-tributylamine complex, with a small amount of methylaluminum dichloride-tributylamine. The crude product is expected to be obtained by vacuum transfer, and to be further purified by sublimation in vacuuo. Trimethylindium is expected in high yield and to contain oxygenated organic and metallic impurities at less than 0.1 ppm as analyzed by FT-NMR and/or ICP-OES techniques.

EXAMPLE 9

Methyl indium dichloride (60 g, 0.30 mol) is dispersed in degassed squalane (250 mL) and to this suspension is added dropwise with stirring the adduct of tri-isopropyl aluminum (47 g, 0.30 mol) with tributylamine (70 mL, 55 g, 0.30 mol). The reaction is expected to be moderately vigorous accompanied by heat generation. Hence adequate cooling of the reaction mass and controlled addition of organoaluminum adduct is expected to be important in successfully carrying out the desired alkyl exchange. The reaction mass is heated to 80 to 90° C. for an hour following the complete addition of reagents. The by-product is expected to be isopropyl aluminum dichloride-tributylamine complex, with a small amount of aluminum trichloride-tributylamine complex. The crude product is expected to be obtained by vacuum transfer, and to be further purified by distillation under reduced pressure. Di-isopropyl methyl indium is expected to be obtained in high yield and contain oxygenated organic and metallic impurities at less than 0.1 ppm as analyzed by FT-NMR and/or ICP-OES techniques.

EXAMPLE 10

To a mixture of methyl aluminum dichloride (45 g, 0.40 mol), dimethylaluminum chloride (37 g, 0.40 mol), and linear alkyl benzene (200 mL) maintained at 70 to 90° C. is added trioctylamine (135 mL, 110 g, 0.42 mol) with rapid stirring and in a dropwise manner. The reaction is expected to proceed gradually to produce trimethyl aluminum and the complex of trichloro aluminum with trioctylamine. Upon completing the addition, the reaction mass is heated to 100° C. for two hours to ensure complete reaction. The by-product is expected to contain a small amount of methylaluminum dichloride-trioctylamine complex. The crude product is expected to be obtained by vacuum transfer, and to be further purified by distillation under reduced pressure using packed distillation column. Trimethylaluminum is expected to be obtained in high yield and to contain oxygenated organic and metallic impurities at less than 0.1 ppm as analyzed by FT-NMR and/or ICP-OES techniques.

EXAMPLE 11

Deposition of an undoped GaAs layer was carried out in a commercial cold-wall, vertical chamber, and inductively heated MOCVD reactor operating at atmospheric pressure and accommodating one wafer per growth. A thin GaAs layer having a thickness of 6 μm was deposited by standard MOCVD technique at 620° C. on a GaAs substrate having a thickness of about 200 μm. The substrate was chemically treated beforehand by standard degreasing techniques. The gallium source was triethylgallium (TEG), and arsine gas was used as the arsenic source. The carrier gas diluent, hydrogen, was used at flow rates to afford V/III ratio (i.e. arsenic/gallium ratio) of 150. The hydride source, arsine, was introduced via a separate line. The reactants were allowed to decompose on heated GaAs substrate at 620° C. The epitaxial layers of GaAs were analyzed by standard van der Pauw Hall-effect measurements of electron mobility and carrier concentration at both 300 and 77 K. Two independent commercial sources (A and B) of semiconductor-grade TEG were used, under identical conditions of film growth, for the comparative evaluation of TEG product that was obtained by the procedure of Example 2. As shown in the following Table, superior electrical properties, i.e. higher electron mobility and lower carrier concentration, were achieved using TEG produced by the procedure of Example 2.

| TEG Source | Growth Reference | V/III Ratio | Growth Temperature (° C.) | 300 K | | 77 K | |
|---|---|---|---|---|---|---|---|
| | | | | Mobility ($cm^2/Vs$) | Carrier Conc. ($cm^{-3}$) | Mobility ($cm^2/Vs$) | Carrier Conc. ($cm^{-3}$) |
| Commercial Source A | 0583 | 150 | 620 | 6,500 | 1.0E14 | 147,000 | 1.0E14 |
| Example 2 | 0585 | 150 | 620 | 7,700 | 6.9E13 | 189,000 | 5.5E13 |
| Commercial Source B | 0587 | 150 | 620 | 7,500 | 1.14E14 | 161,000 | 1.0E14 |

EXAMPLE 12

To a suspension of indium metal (5 g, 44 mmol) in squalane (20 mL), stirred in a flask equipped with a condenser and magnetic stirrer, was added iodomethane (9.3 g, 66 mmol) in a dropwise manner to synthesize methyl indium sesquiiodide. The reaction was carried out under nitrogen atmosphere. The reaction was found to initiate only after heating the reaction mass to 110° C. The heating was continued for two hours and the contents were allowed to cool down. The reaction mixture is analyzed by $^1$H FT-NMR and shows the presence of trimethylindium. An adduct of trimethylaluminum (4.7 g, 66 mmol) and tripropyl amine (9.4 g, 66 mmol) was added to the reaction mixture by using siphoning technique in a dropwise manner. The reaction mixture was heated to 90° C. for one hour. An attempt was made to isolate the product using vacuum transfer. The crude product was analyzed by FT-NMR to detect any trimethylindium that may have been formed. Analysis showed the crude product to be comprised of trimethylindium, excess trimethylaluminum-tripropylamine adduct, and squalane.

COMPARATIVE EXAMPLE

To a suspension of indium metal (5 g, 44 mmol) in linear alkyl benzene (20 mL), stirred in a flask equipped with a condenser and magnetic stirrer, was added iodoethane (10 g, 64 mmol) in a dropwise manner to synthesize ethyl indium sesquiiodide. The reaction was carried out under nitrogen atmosphere. The reaction was found to initiate only after heating the reaction mass to 110° C. The heating was continued for two hours and the contents were allowed to cool down. Trimethylaluminum (3 g, 42 mmol) was added to the reaction mixture by using siphoning technique in a dropwise manner. An attempt was made to isolate the product using vacuum transfer. The crude product was analyzed by FT-NMR to detect any trimethylindium that may have been formed. Analysis showed the crude product to be comprised of trimethylaluminum, iodoethane and linear alkyl benzene. No trimethylindium was detected in the crude product.

What is claimed is:

1. A method of preparing an organometallic compound comprising the steps of: reacting a compound of the formula $R^1_a M1^{b'} Y^1_{c'}$ wherein each $R^1$ is independently a ($C_1$–$C_{10}$) organic radical, M1 is a Group IIB or IIIA metal, each $Y^1$ is independently a ($C_1$–$C_4$) carboxylate or halogen, a'=0–2, b' is the valence of M1, c'=1–3, and a'+c'=b', with a compound of the formula $R^2_x M2 Y^2_{3-x}$ wherein each $R^2$ is independently a ($C_1$–$C_{10}$) organic radical, M2 is a Group IIIA metal, each $Y^2$ is independently a ($C_1$–$C_4$) carboxylate or halogen, x=1–3, in the presence of a tertiary amine, a tertiary phosphine or a mixture of a tertiary amine and a tertiary phosphine, wherein an electronegativity of M1 ≧ an electronegativity of M2.

2. The method of claim 1 wherein Y is halogen.

3. The method of claim 1 wherein the reaction is performed in the presence of an organic solvent.

4. The method of claim 3 wherein M1 and M2 are both aluminum.

5. The method of claim 1 further comprising a heating step.

6. The method of claim 1 wherein each $R^1$ and each $R^2$ are ($C_1$–$C_6$)alkyl.

7. The method of claim 1 wherein the tertiary amine has a formula $NR^4 R^5 R^6$, wherein $R^4$, $R^5$ and $R^6$ are independently chosen from ($C_1$–$C_6$)alkyl, di($C_1$–$C_6$)alkylamino-substituted ($C_1$–$C_6$)alkyl, and phenyl; and wherein $R^4$ and $R^5$ may be taken together along with the nitrogen to which they are attached to form a 5–7 membered heterocyclic ring.

8. The method of claim 7 wherein a trialkyl aluminum and an aluminum trihalide are produced.

9. The method of claim 1 wherein the organometallic compound has the formula $R_a M^b Y_c$, wherein each R is independently a ($C_1$–$C_{10}$) organic radical, M=M1, Y=$Y^1$, a=1–3, b is the valence of M, c=0–2, and a+c=b.

10. The method of claim 9 wherein M is indium, gallium or aluminum.

11. The method of claim 9, wherein M is a Group IIIA metal, Y=halogen and c ≠0, and further comprising the step of contacting the organometallic compound with a reducing agent in an organic solvent, optionally in the presence of a tertiary amine, a tertiary phosphine or a mixture of a tertiary amine and a tertiary phosphine, to provide a Group IIIA metal hydride compound.

12. The method of claim 1 wherein the tertiary phosphine has the formula $R^7 R^8 R^9 P$, where $R^7$, $R^8$, and $R^9$ are independently chosen from ($C_1$–$C_6$)alkyl, phenyl and ($C_1$–$C_6$) alkyl-substituted phenyl.

13. A method of preparing an organometallic compound comprising the steps of: reacting a compound of the formula $R^1_a M1^{b'} Y^1_{c'}$ wherein each $R^1$ is independently a ($C_1$–$C_{10}$) organic radical, M1 is a Group IIB or IIIA metal, each $Y^1$ is independently a ($C_1$–$C_4$) carboxylate or halogen, a'=0–2, b' is the valence of M1, c'=1–3, and a'+c'=b', with a compound of the formula $R^2_x M2 Y^2_{3-x}$ wherein each $R^2$ is independently a ($C_1$–$C_{10}$) organic radical, M2 is a Group IIIA metal, each $Y^2$ is independently a ($C_1$–$C_4$) carboxylate or halogen, and x=1–3, in the presence of a tertiary amine, a tertiary phosphine or a mixture of a tertiary amine and a tertiary phosphine, wherein an electronegativity of M1 ≧ an electronegativity of M2; wherein the organometallic compound has the formula $R_a M^b Y_c$, wherein each R is independently a ($C_1$–$C_{10}$) organic radical, M=M1, Y=$Y^1$, a=1–3, b is the valence of M, c=0–2, and a+c=b; and wherein the organometallic compound has ≦0.5 ppm of metallic impurities chosen from silicon, germanium and tin.

14. The method of claim 13 wherein the reaction is performed in the presence of an organic solvent.

15. The method of claim 13 further comprising a heating step.

* * * * *